US00PP26235P2

(12) United States Plant Patent
Steffen

(10) Patent No.: US PP26,235 P2
(45) Date of Patent: Dec. 15, 2015

(54) ***ANGELONIA* PLANT NAMED 'LOTRAWHI'**

(50) Latin Name: *Angelonia hybrida*
Varietal Denomination: Lotrawhi

(71) Applicant: Elke Steffen, Erfurt (DE)

(72) Inventor: Elke Steffen, Erfurt (DE)

(73) Assignee: Elsner pac Jungpflanzen Gbr, Dresden (DE)

( * ) Notice: Subject to any disclaimer, the term of this patent is extended or adjusted under 35 U.S.C. 154(b) by 28 days.

(21) Appl. No.: 13/999,883

(22) Filed: Apr. 1, 2014

(51) Int. Cl.
*A01H 5/02* (2006.01)

(52) U.S. Cl.
USPC ..... Plt./404

(58) Field of Classification Search
USPC ..... Plt./404
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Angelonia* plant named 'Lotrawhi' characterized by its trailing plant habit; freely branching habit; early and freely flowering habit; large white-colored flowers; and good garden performance.

2 Drawing Sheets

Botanical designation: *Angelonia hybrida.*
Cultivar denomination: 'LOTRAWHI'.

BACKGROUND OF THE INVENTION

The present invention relates to a new and distinct cultivar of *Angelonia* plant, botanically known as *Angelonia hybrida* and hereinafter referred to by the name 'Lotrawhi'.

The new *Angelonia* plant is a product of a planned breeding program conducted by the Inventor in Dresden, Germany. The objective of the breeding program is to create new trailing and freely-flowering *Angelonia* plants with attractive flower coloration.

The new *Angelonia* plant originated from a cross-pollination made by the Inventor during the summer of 2009 in Dresden, Germany of two unnamed proprietary selections of *Angelonia hybrida*, not patented. The new *Angelonia* plant was discovered and selected by the Inventor as a single flowering plant within the progeny of the stated cross-pollination in a controlled greenhouse environment in Dresden, Germany during the summer of 2010.

Asexual reproduction of the new *Angelonia* plant by cuttings in a controlled greenhouse environment in Dresden, Germany since August, 2010 has shown that the unique features of this new *Angelonia* plant are stable and reproduced true to type in successive generations.

SUMMARY OF THE INVENTION

Plants of the new *Angelonia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Lotrawhi'. These characteristics in combination distinguish 'Lotrawhi' as a new and distinct *Angelonia* plant:

1. Trailing plant habit.
2. Freely branching habit.
3. Early and freely flowering habit.
4. Large white-colored flowers.
5. Good garden performance.

Plants of the new *Angelonia* differ from plants of the parent selections primarily in plant and flowering habit as plants of the new *Angelonia* are more freely branching and freely flowering than plants of the parent selections.

Plants of the new *Angelonia* can be compared to plants of *Angelonia* hybrid 'Adewhi', disclosed in U.S. Plant Pat. No. 21,996. In side-by-side comparisons conducted in Dresden, Germany, plants of the new *Angelonia* and 'Adewhi' differed in the following characteristics:

1. Plants of the new *Angelonia* had a trailing plant habit whereas plants of 'Adewhi' had an upright plant habit.
2. Plants of the new *Angelonia* were more freely branching than plants of 'Adewhi'.
3. Plants of the new *Angelonia* had narrower leaves than plants of 'Adewhi'.
4. Plants of the new *Angelonia* had smaller flowers than 'Adewhi'.

BRIEF DESCRIPTION OF THE PHOTOGRAPHS

The accompanying colored photographs illustrate the overall appearance of the new *Angelonia* plant showing the colors as true as it is reasonably possible to obtain in colored reproductions of this type. Colors in the photographs may differ slightly from the color values cited in the detailed botanical description which accurately describe the colors of the new *Angelonia* plant.

The photograph on the first sheet comprises a side perspective view of a typical flowering plant of 'Lotrawhi' grown in a ground bed.

The photograph on the second sheet comprises a side perspective view of a typical flowering plant of 'Lotrawhi' grown in a container.

DETAILED BOTANICAL DESCRIPTION

Plants used for the aforementioned photographs and the following observations, measurements and values were grown during the summer and autumn in 13-cm containers in a glass-covered greenhouse in Dresden, Germany and under cultural practices typical of commercial *Angelonia* production. During the production of the plants, day temperatures were about 20° C., night temperatures were about 16° C. and light levels ranged from 15 kilolux to 100 kilolux. Plants were pinched two times, two and six weeks after planting. Plants were five months old when the description was taken and six months old when the photographs were taken. In the following description, color references are made to The Royal Horticultural Society Colour Chart, 1995 Edition, except where general terms of ordinary dictionary significance are used.

Botanical classification: *Angelonia hybrida* 'Lotrawhi'.

Parentage:

*Female, or seed, parent*.—Unnamed proprietary selection of *Angelonia hybrida*, not patented.

*Male, or pollen, parent*.—Unnamed proprietary selection of *Angelonia hybrida*, not patented.

Propagation:

*Type*.—By cuttings.

*Time to initiate roots*.—About 20 days at temperatures about 20° C.

*Time to produce a rooted young plant*.—About four weeks at temperatures about 20° C.

*Root description*.—Fine, fibrous; white in color.

*Rooting habit*.—Freely branching; moderately dense.

Plant description:

*Plant form and growth habit*.—Herbaceous perennial; trailing plant habit; very broad inverted triangle; freely branching habit; when pinched, about ten to twelve lateral branches develop per plant; moderately vigorous growth habit.

*Plant height*.—About 10 to 15 cm.

*Plant width* (*spread*).—About 40 cm.

*Lateral branches*.—Length: About 20 cm to 25 cm. Diameter: About 1 mm to 2 mm. Internode length: About 1 cm to 2 cm. Strength: Fine to moderately strong. Texture: Slightly pubescent. Color: Close to 144A.

Leaf description:

*Arrangement*.—Opposite, decussate; simple; sessile.

*Length*.—About 2 cm to 8 cm.

*Width*.—About 5 mm to 10 mm.

*Shape*.—Lanceolate to oblong.

*Apex*.—Acute.

*Base*.—Attenuate.

*Margin*.—Serrate.

*Texture, upper and lower surfaces*.—Smooth, glabrous.

*Venation pattern*.—Pinnate.

*Color*.—Developing and fully expanded leaves, upper surface: Close to 137C; venation, close to 137C. Developing and fully expanded leaves, lower surface: Close to 137D; venation, close to 145C.

Flower description:

*Flower type and flowering habit*.—Single flowers arranged in terminal racemes; flowers face mostly outwardly; freely flowering habit; full dense inflorescences.

*Fragrance*.—None detected.

*Natural flowering season*.—Early flowering habit, plants begin flowering about nine to ten weeks after planting; in the garden, flowering is continuous from mid-May until frost in Central Europe.

*Postproduction longevity*.—Flowers last about 20 days on the plant; flowers not persistent.

*Flower buds*.—Height: About 3 mm to 5 mm. Diameter: About 3 mm to 5 mm. Shape: Globose. Color: Close to 137C.

*Inflorescence height*.—About 20 cm to 25 cm.

*Inflorescence diameter*.—About 5 cm to 6 cm.

*Flower size*.—About 2 cm by 2 cm.

*Flower depth*.—About 5 mm to 10 mm.

*Petals*.—Quantity per flower: Typically five in a single whorl; petals fused at the base into a tubular throat. Length: About 8 mm to 10 mm. Width: About 8 mm to 10 mm. Shape: Roughly spatulate. Apex: Rounded. Margin: Entire, undulate. Texture, upper and lower surfaces: Smooth, glabrous; velvety. Color: When opening and fully opened, upper surface: Close to 155D. When opening and fully opened, lower surface: Close to 155D. Throat: Close to 155D.

*Sepals*.—Quantity per flower: Typically five in a single whorl. Length: About 4 mm. Width: About 2 mm. Shape: Ovate. Apex: Acute. Margin: Entire. Texture, upper and lower surfaces: Smooth, glabrous. Color, upper surface: Close to 137A. Color, lower surface: Close to 137B.

*Pedicels*.—Length: About 1 cm to 2 cm. Diameter: About 1 mm. Angle: Outward to slightly upright, less than 90° from vertical. Strength: Moderately strong; flexible. Texture: Slightly pubescent. Color: Close to 146B.

*Reproductive organs*.—Stamens: Quantity per flower: Typically four. Filament length: About 3 mm. Filament color: Close to 155C. Anther shape: Elliptic. Anther length: About 2 mm. Anther color: Brown to grey. Pollen amount: Moderate. Pollen color: Close to 155D. Pistils: Quantity per flower: One. Pistil length: About 3 mm. Stigma shape: Tapering. Stigma color: Close to 155D. Style length: About 3 mm. Style color: Close to 155D. Ovary color: Close to 142B.

*Fruits*.—Length: About 5 mm. Diameter: About 5 mm. Color: Close to 165C.

*Seeds*.—Quantity per flower: About 30 to 50. Length: Less than 1 mm. Diameter: Less than 1 mm. Color: Light brown.

Disease & pest resistance: Plants of the new *Angelonia* have not been noted to be resistant to pathogens and pests common to *Angelonia* plants.

Garden performance: Plants of the new *Angelonia* have been observed to have good garden performance and tolerate rain, wind and temperatures ranging from about 1° C. to 30° C.

It is claimed:

1. A new and distinct *Angelonia* plant named 'Lotrawhi' as illustrated and described.

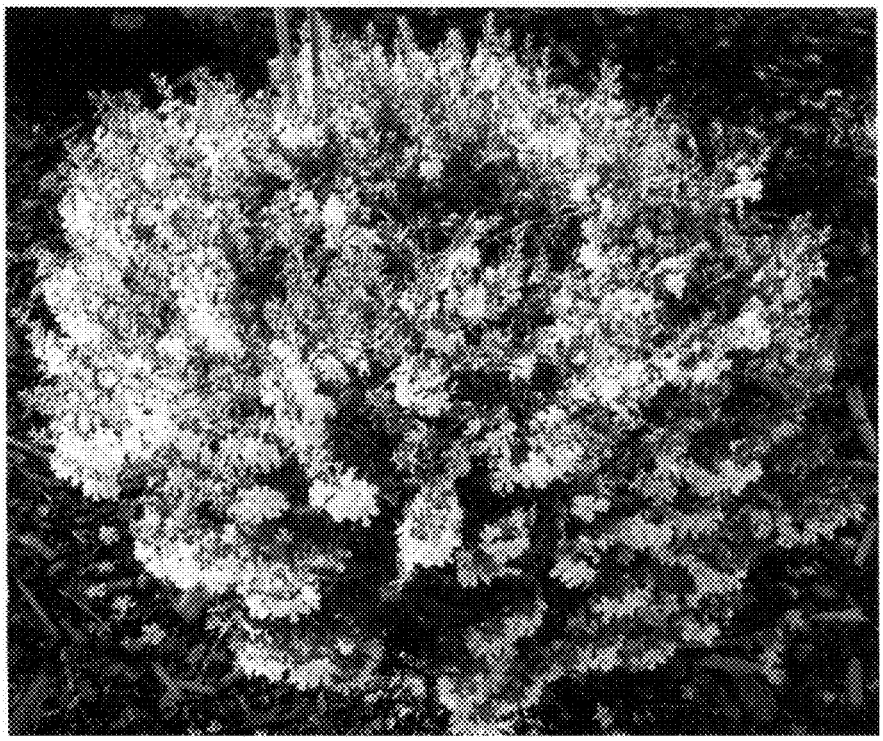

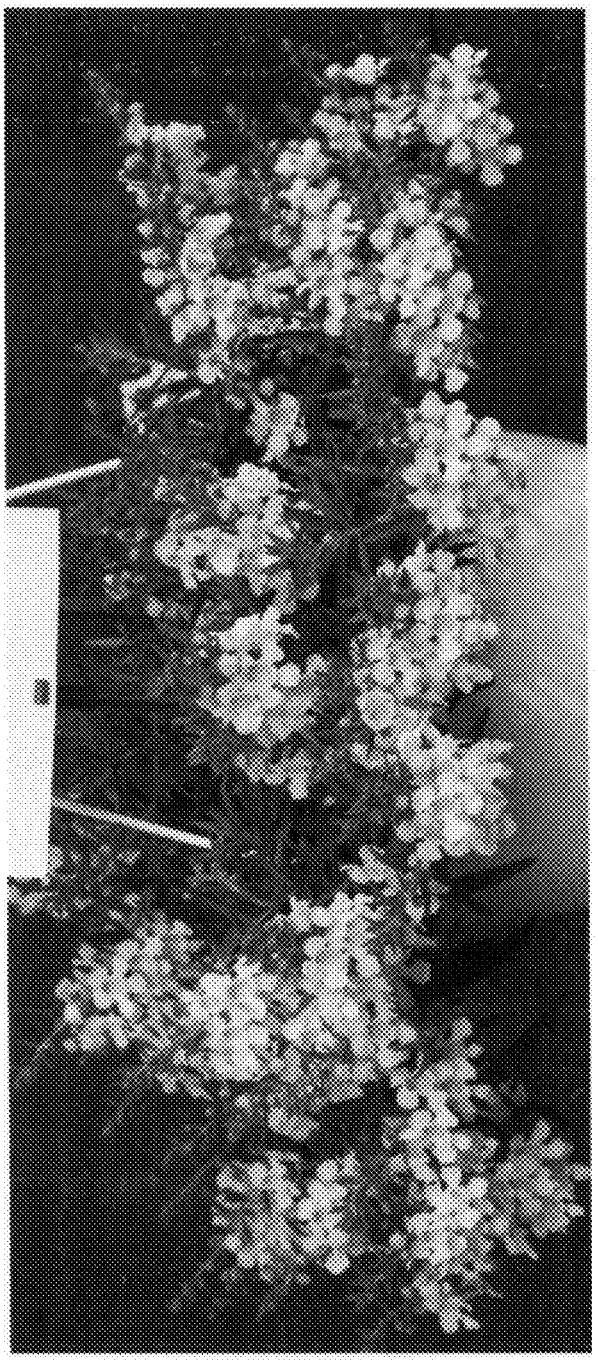

* * * * *